(12) United States Patent
Feldman et al.

(10) Patent No.: US 10,368,776 B2
(45) Date of Patent: *Aug. 6, 2019

(54) METHOD AND APPARATUS FOR DETERMINING CARDIAC PERFORMANCE IN A PATIENT WITH A CONDUCTANCE CATHETER

(71) Applicants: Marc D. Feldman, San Antonio, TX (US); Jonathan W. Valvano, Austin, TX (US); John A. Pearce, Austin, TX (US); Chia-Ling Wei, Tainan (TW)

(72) Inventors: Marc D. Feldman, San Antonio, TX (US); Jonathan W. Valvano, Austin, TX (US); John A. Pearce, Austin, TX (US); Chia-Ling Wei, Tainan (TW)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/816,048

(22) Filed: Nov. 17, 2017

(65) Prior Publication Data
US 2018/0070851 A1    Mar. 15, 2018

Related U.S. Application Data

(60) Continuation of application No. 15/193,931, filed on Jun. 27, 2016, now Pat. No. 9,820,674, which is a continuation of application No. 14/589,603, filed on Jan. 5, 2015, now Pat. No. 9,380,946, which is a continuation of application No. 13/066,201, filed on Apr. 8, 2011, now Pat. No. 8,929,976, which is a division of application No. 10/568,912, filed as application No. PCT/US2004/028573 on Sep. 3, 2004, now Pat. No. 7,925,335.

(60) Provisional application No. 60/501,749, filed on Sep. 9, 2003.

(51) Int. Cl.
| | | |
|---|---|---|
| *A61B 5/053* | (2006.01) | |
| *A61B 5/02* | (2006.01) | |
| *A61B 5/0215* | (2006.01) | |
| *A61B 5/029* | (2006.01) | |

(52) U.S. Cl.
CPC ........ *A61B 5/0538* (2013.01); *A61B 5/02007* (2013.01); *A61B 5/029* (2013.01); *A61B 5/0215* (2013.01); *A61B 5/053* (2013.01)

(58) Field of Classification Search
None
See application file for complete search history.

(56) References Cited

U.S. PATENT DOCUMENTS

| | | | | |
|---|---|---|---|---|
| 4,951,682 A | * | 8/1990 | Petre | ...................... A61B 5/029 |
| | | | | 600/522 |
| 6,494,832 B1 | * | 12/2002 | Feldman | .............. A61B 5/0422 |
| | | | | 600/301 |

* cited by examiner

*Primary Examiner* — Brian T Gedeon
(74) *Attorney, Agent, or Firm* — Ansel M. Schwartz (57) ABSTRACT

An apparatus for determining cardiac performance in the patient includes a plurality of electrodes adapted to be placed in the patient and in communication with a heart chamber of the patient for measuring conductance and blood volume in the heart chamber of the patient; and a processor for determining instantaneous volume of the ventricle based on measurement of complex admittance at a plurality of frequencies to identify mechanical strength of the chamber, the processor in communication with the electrodes. A method for determining cardiac performance in a patient.

14 Claims, 5 Drawing Sheets

METHOD AND APPARATUS FOR DETERMINING CARDIAC PERFORMANCE IN A PATIENT WITH A CONDUCTANCE CATHETER

CROSS-REFERENCE TO RELATED APPLICATIONS

This is a continuation of U.S. patent application Ser. No. 15/193,931 filed Jun. 27, 2016, now U.S. Pat. No. 9,820,674, which is a continuation of U.S. patent application Ser. No. 14/589,603 filed Jan. 5, 2015, now U.S. Pat. No. 9,380,946, which is a continuation of U.S. patent application Ser. No. 13/066,201 filed Apr. 8, 2011, now U.S. Pat. No. 8,929,976, which is a divisional of U.S. patent application Ser. No. 10/568,912 filed Nov. 1, 2007, now U.S. Pat. No. 7,925,335 issued Apr. 12, 2011, which is a 371 of international application PCT/US04/28573 filed Sep. 3, 2004, which is an international application of U.S. provisional application Ser. No. 60/501,749 filed Sep. 9, 2003, all of which are incorporated by reference herein.

FIELD OF THE INVENTION

The present invention is related to measuring instantaneous ventricular volume in the heart of a patient. More specifically, the present invention is related to measuring instantaneous ventricular volume in the heart of a patient by removing the contributor to conductance of muscle, and applying a non-linear relationship to the measured conductance and the volume of blood in the heart.

BACKGROUND OF THE INVENTION

Measurements of electrical conductance using a tetrapolar admittance catheter are used to estimate instantaneous ventricular volume in animals and humans. The measurements of volume are plotted against ventricular pressure to determine several important parameters of cardiac physiologic function. A significant source of uncertainty in the measurement is parallel conductance due to current in the ventricular muscle. The estimated volume is larger than the blood volume alone, which is required for the diagnostic measurement. Furthermore, presently, a linear relationship between conductance and estimated volume is used to calibrate the measurements. The actual relationship is substantially non-linear.

The invention comprises an improved method for estimating instantaneous blood volume in a ventricle by subtracting the muscle contribution form the total conductance measured. The method relies on measuring the complex admittance, rather than apparent conductance (admittance magnitude), as is presently done. Briefly, the improvement consists of measuring the phase angle in addition to admittance magnitude and then directly subtracting the muscle component from the combined measurement, thereby improving the estimate of instantaneous blood volume. The technique works because the electrical properties of muscle are frequency-dependent, while those of blood are not. We propose this calibration technique as a substantial improvement in clinical and research instrumentation calibration methods.

The invention comprises an improved method for estimating instantaneous volume of a ventricle by applying a nonlinear relationship between the measured conductance and the volume of blood in the surrounding space. The nonlinear calibration relation has been determined from experiments and numerical model studies. This calibration technique is a substantial improvement in clinical and research instrumentation calibration methods.

SUMMARY OF THE INVENTION

The present invention pertains to an apparatus for determining cardiac performance in the patient. The apparatus comprises a conductance catheter for measuring conductance and blood volume in a heart chamber of the patient. The apparatus comprises a processor for determining instantaneous volume of the ventricle by applying a non-linear relationship between the measured conductance and the volume of blood in the heart chamber to identify mechanical strength of the chamber. The processor is in communication with the conductance catheter.

The present invention pertains to a method for determining cardiac performance in the patient. The method comprises the steps of measuring conductance and blood volume in a heart chamber of the patient with a conductance catheter. There is the step of determining instantaneous volume of the ventricle by applying a non-linear relationship between the measured conductance and the volume of blood in the heart chamber to identify mechanical strength of the chamber with a processor. The processor in communication with the conductance catheter.

The present invention pertains to an apparatus for determining cardiac performance in a patient. The apparatus comprises a conductance catheter for measuring conductance in a heart chamber of the patient, where the conductance includes contributions from blood and muscle with respect to the heart chamber. The apparatus comprises a processor for determining instantaneous volume of the heart chamber by removing the muscle contribution from the conductance. The processor is in communication with the conductance catheter.

The present invention pertains to a method for determining cardiac performance in a patient. The method comprises the steps of measuring conductance in a heart chamber of the patient with a conductance catheter, where the conductance includes contributions from blood and muscle with respect to the heart chamber. There is the step of determining instantaneous volume of the heart chamber by removing the muscle contribution from the conductance with a processor, the processor in communication with the conductance catheter.

The present invention pertains to an apparatus for determining cardiac performance in the patient. The apparatus comprises a conductance catheter having measuring electrodes for measuring conductance in a heart chamber of the patient. The apparatus comprises a processor for determining instantaneous volume of the heart chamber according to $$Vol(t) = [\beta(G)]\left[\frac{L^2}{\sigma_b}\right][Y(t) - Y_p]$$

where: $\beta(G)$=the field geometry calibration function (dimensionless), $Y(t)$=the measured combined admittance, $\sigma_b$ is blood conductivity, $L$ is distance between measuring electrodes, and $Y_p$=the parallel leakage admittance, dominated by cardiac muscle, the processor in communication with the conductance catheter.

The present invention pertains to a method for determining cardiac performance in the patient. The method comprises the steps of measuring conductance and blood volume in a heart chamber of the patient with a conductance catheter having measuring electrodes. There is the step of determining instantaneous volume of the ventricle according to $$Vol(t) = [\beta(G)]\left[\frac{L^2}{\sigma_b}\right][Y(t) - Y_p]$$

where: $\beta(G)$=the field geometry calibration function (dimensionless), $Y(t)$=the measured combined admittance, $\sigma_b$ is blood conductivity, L is distance between measuring electrodes, and $Y_p$=the parallel leakage admittance, dominated by cardiac muscle, to identify mechanical strength of the chamber with a processor. The processor is in communication with the conductance catheter.

BRIEF DESCRIPTION OF THE DRAWINGS

In the accompanying drawings, the preferred embodiment of the invention and preferred methods of practicing the invention are illustrated in which.

DETAILED DESCRIPTION

Figure 7:
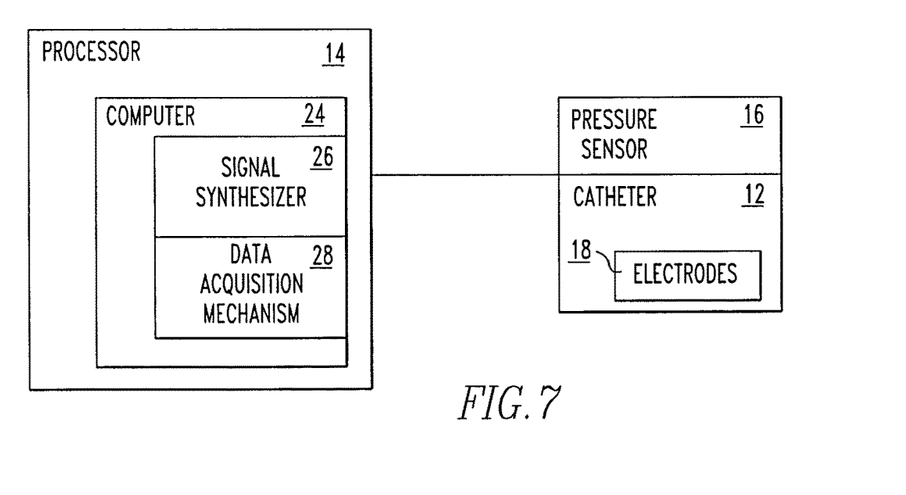
FIG. 7 is a schematic representation of the apparatus of the present invention.

Referring now to the drawings wherein like reference numerals refer to similar or identical parts throughout the several views, and more specifically to FIG. 7 thereof, there is shown an apparatus for determining cardiac performance in the patient. The apparatus comprises a conductance catheter 12 for measuring conductance and blood volume in a heart chamber of the patient. The apparatus comprises a processor 14 for determining instantaneous volume of the ventricle by applying a non-linear relationship between the measured conductance and the volume of blood in the heart chamber to identify mechanical strength of the chamber. The processor 14 is in communication with the conductance catheter 12.

Preferably, the apparatus includes a pressure sensor 16 for measuring instantaneous pressure of the heart chamber in communication with the processor 14. The processor 14 preferably produces a plurality of desired wave forms at desired frequencies for the conductance catheter 12. Preferably, the processor 14 produces the plurality of desired wave forms at desired frequencies simultaneously, and the processor 14 separates the plurality of desired wave forms at desired frequencies the processor 14 receives from the conductance catheter 12. The conductance catheter 12 preferably includes a plurality of electrodes 18 to measure a least one segmental volume of the heart chamber.

Preferably, the non-linear relationship depends on a number of the electrodes 18, dimensions and spacing of the electrodes 18, and an electrical conductivity of a medium in which the electrodes 18 of the catheter 12 are disposed. The non-linear relationship may be expressed as (or a substantially similar mathematical form):

$$\beta(G)(\sigma=0.928 \text{ S/m})=1+1.774(10^{7\ 481\times10^{-4}(G-2057)})$$

Alternatively, an approximate calibration factor may be used with similar accuracy of the form (or its mathematical equivalent):

$$\beta \cong e^{\gamma G_b^2}$$

where: G is the measured conductance (S), the calculations have been corrected to the conductivity of whole blood at body temperature (0.928 S/m), and 2057 is the asymptotic conductance in μS when the cuvette is filled with a large volume of whole blood. Preferably, $$Vol(t) = [\beta(G)]\left[\frac{L^2}{\sigma_b}\right][Y(t) - Y_p]$$

where: $\beta(G)$=the field geometry calibration function (dimensionless), $Y(t)$=the measured combined admittance, $\sigma_b$ is blood conductivity, L is distance between measuring electrodes, and $Y_p$=the parallel leakage admittance, dominated by cardiac muscle.

The pressure sensor 16 preferably is in contact with the conductance catheter 12 to measure ventricular pressure in the chamber. Preferably, the plurality of electrodes 18 includes intermediate electrodes 20 to measure the instantaneous voltage signal from the heart, and outer electrodes 22 to which a current is applied from the processor 14. The pressure sensor 16 preferably is disposed between the intermediate electrodes 20. Preferably, the processor 14 includes a computer 24 with a signal synthesizer 26 which produces the plurality of desired wave forms at desired frequencies and a data acquisition mechanism 28 for receiving and separating the plurality of desired wave forms at desired frequencies. The computer 24 preferably converts conductance into a volume. Preferably, the computer 24 produces a drive signal having a plurality of desired wave forms at desired frequencies to drive the conductance catheter 12.

The present invention pertains to a method for determining cardiac performance in the patient. The method comprises the steps of measuring conductance and blood volume in a heart chamber of the patient with a conductance catheter 12. There is the step of determining instantaneous volume of the ventricle by applying a non-linear relationship between the measured conductance and the volume of blood in the heart chamber to identify mechanical strength of the chamber with a processor 14. The processor 14 in communication with the conductance catheter 12.

Preferably, there is the step of measuring instantaneous pressure of the heart chamber with a pressure sensor 16 in communication with the processor 14. There is preferably the step of producing a plurality of desired wave forms at desired frequencies for the conductance catheter 12. Preferably, the producing step includes the step of producing the plurality of desired wave forms at desired frequencies simultaneously, and including the step of the processor 14 separating the plurality of desired wave forms at desired frequencies the processor 14 received from the conductance catheter 12. The producing step preferably includes the step of producing with the processor 14 the plurality of desired wave forms at desired frequencies simultaneously.

Preferably, the determining step includes the step of applying the non-linear relationship according to the following (or its mathematical equivalent):

$$\beta(G)(\sigma=0.928 \text{ S/m}) = 1 + 1.774(10^{7\ 481\times10^{-4}(G-2057)})$$

where: G is the measured conductance (S), the calculations have been corrected to the conductivity of whole blood at body temperature (0.928 S/m), and 2057 is the asymptotic conductance in μS when the cuvette is filled with a large volume of whole blood. Or, alternatively, an approximate geometry calibration factor may be used:

$$\beta = e^{\gamma[Gb]^2}$$

where α is determined experimentally or from mathematical calculations or numerical models.

The determining step preferably includes the step of determining instantaneous volume according to $$Vol(t) = [\beta(G)]\left[\frac{L^2}{\sigma_b}\right][Y(t) - Y_p]$$

where: β(G)=the field geometry calibration function (dimensionless), Y(t)=the measured combined admittance, $\sigma_b$ is blood conductivity, L is distance between measuring electrodes, and $Y_p$=the parallel leakage admittance, dominated by cardiac muscle.

Preferably, the step of measuring instantaneous pressure includes the step of measuring instantaneous pressure with the pressure sensor 16 in contact with the conductance catheter 12 to measure the ventricular pressure in the chamber. The measuring step preferably includes the step of measuring at least one segmental volume of the heart chamber with a plurality of electrodes 18 on the conductance catheter 12. Preferably, the measuring step includes the steps of applying a current to outer electrodes 22 of the plurality of electrodes 18 from the processor 14, and measuring an instantaneous voltage signal from the heart with intermediate electrodes 20 of the plurality of electrodes 18.

The step of measuring instantaneous pressure preferably includes the step of measuring instantaneous pressure with the pressure sensor 16 disposed between the intermediate electrodes 20 and the outer electrodes 22. Preferably, the producing with the processor 14 step includes the step of producing with a signal synthesizer 26 of a computer 24 the plurality of desired wave forms at desired frequencies, and the processor 14 separating step includes the step of receiving and separating the plurality of desired wave forms at desired frequencies with a data acquisition mechanism 28 of the computer 24. There is preferably the step of converting conductance into a volume with the computer 24. Preferably, there is the step of producing with the computer 24 a drive signal having the plurality of desired wave forms at desired frequencies to drive the conductance catheter 12.

The present invention pertains to an apparatus for determining cardiac performance in a patient. The apparatus comprises a conductance catheter 12 for measuring conductance in a heart chamber of the patient, where the conductance includes contributions from blood and muscle with respect to the heart chamber. The apparatus comprises a processor 14 for determining instantaneous volume of the heart chamber by removing the muscle contribution from the conductance. The processor 14 is in communication with the conductance catheter 12.

Preferably, the apparatus includes a pressure sensor 16 for measuring instantaneous pressure of the heart chamber in communication with the processor 14. The processor 14 preferably produces a plurality of desired wave forms at desired frequencies for the conductance catheter 12. Preferably, the processor 14 produces the plurality of desired wave forms at desired frequencies simultaneously, and the processor 14 separates the plurality of desired wave forms at desired frequencies the processor 14 receives from the conductance catheter 12. The processor 14 preferably measures complex admittance with the conductance catheter 12 to identify the muscle contribution.

Preferably, the complex admittance is defined as $$Y_p = Gm + j\omega Cm \text{ (Y subscript } p)$$

where

Cm=capacitance component of muscle (F=Farads) (C subscript m)

ω=angular frequency (radians/second) (greek "omega"=2 pi f)

Gm=conductance of muscle (S=Siemens) (G subscript m). The conductance preferably is defined as $$Y(t) = Gb + Gm + j\omega Cm$$

where Gb=conductance of blood (S) (G subscript b).

The present invention pertains to a method for determining cardiac performance in a patient. The method comprises the steps of measuring conductance in a heart chamber of the patient with a conductance catheter 12, where the conductance includes contributions from blood and muscle with respect to the heart chamber. There is the step of determining instantaneous volume of the heart chamber by removing the muscle contribution from the conductance with a processor 14, the processor 14 in communication with the conductance catheter 12.

Preferably, there is the step of measuring instantaneous pressure of the heart chamber with a pressure sensor 16 in communication with the processor 14. There is preferably the step of producing a plurality of desired wave forms at desired frequencies for the conductance catheter 12. Preferably, the producing step includes the step of producing the plurality of desired wave forms at desired frequencies simultaneously, and including the step of the processor 14 separating the plurality of desired wave forms at desired frequencies the processor 14 received from the conductance catheter 12. The producing step preferably includes the step of producing with the processor 14 the plurality of desired wave forms at desired frequencies simultaneously. Preferably, there is the step of measuring complex admittance with the conductance catheter 12 to identify the muscle contribution.

The measuring the complex admittance step preferably includes the step of measuring the complex admittance according to $$Yp = Gm + j\omega Cm \text{ (Y subscript } p)$$

where

Cm=capacitance component of muscle (F=Farads) (C subscript m)

ω=angular frequency (radians/second) (greek "omega"=2 pi f)

Gm=conductance of muscle (S=Siemens) (G subscript m).

Preferably, the determining step includes the step of determining instantaneous volume based on conductance defined as $$Y(t) = Gb + Gm + j\omega Cm \quad (5)$$

where Gb=conductance of blood (S) (G subscript b).

The present invention pertains to an apparatus for determining cardiac performance in the patient. The apparatus comprises a conductance catheter 12 for measuring conductance in a heart chamber of the patient. The apparatus comprises a processor 14 for determining instantaneous volume of the heart chamber according to $$Vol(t) = [\beta(G)]\left[\frac{L^2}{\sigma_b}\right][Y(t) - Y_p]$$

where: $\beta(G)$=the field geometry calibration function (dimensionless), $Y(t)$=the measured combined admittance, $\sigma_b$ is blood conductivity, L is distance between measuring electrodes, and $Y_p$=the parallel leakage admittance, dominated by cardiac muscle, the processor 14 in communication with the conductance catheter 12.

The present invention pertains to a method for determining cardiac performance in the patient. The method comprises the steps of measuring conductance and blood volume in a heart chamber of the patient with a conductance catheter 12. There is the step of determining instantaneous volume of the ventricle according to $$Vol(t) = [\beta(G)]\left[\frac{L^2}{\sigma_b}\right][Y(t) - Y_p]$$

where: $\beta(G)$=the field geometry calibration function (dimensionless), $Y(t)$=the measured combined admittance, $\sigma_b$ is blood conductivity, L is distance between measuring electrodes, and $Y_p$=the parallel leakage admittance, dominated by cardiac muscle, to identify mechanical strength of the chamber with a processor 14. The processor 14 is in communication with the conductance catheter 12.

The classic means to determine left ventricular pressure-volume (PV) relationships in patients on a beat-by-beat basis is through the use of the conductance (volume) catheter 12. The electric field that it creates in the human left ventricle at the time of heart catheterization is the only technology capable of measuring instantaneous left ventricular volume during maneuvers such as transient occlusion of the inferior vena cava. Such maneuvers allow determination of the wealth of information available from the PV plane including: end-systolic elastance, diastolic compliance, and effective arterial elastance. However, use of conductance technology in patients with dilated hearts whose LV volumes can range from 200 to 500 ml has been problematic.

Figure 1:
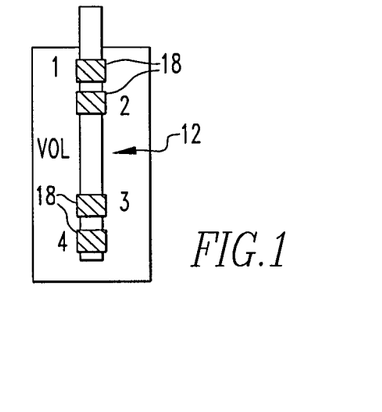
FIG. 1 shows a four electrode catheter in volume cuvette.

The G-V method measures the conductance between electrodes 18 located in the LV and aorta. A minimum of four electrodes 18 is required to prevent the series impedance of the electrode-electrolyte interfaces from distorting the measurement. Typically, the two current source-sink electrodes are located in the aorta and in the LV near the apex (electrodes 1 and 4 in FIG. 1). The potential difference between the potential measuring electrodes (2 and 3) is used to calculate the conductance: G=I/V. The governing assumption is that the current density field is sufficiently uniform that the volume and conductance are simply related by Baan's equation [1]:

$$Vol(t) = \left[\frac{1}{\alpha}\right]\left[\frac{L^2}{\sigma_b}\right][G(t) - G_p] \quad (1)$$

where: $\alpha$ is the geometry factor (a dimensionless constant), L is the center-to-center distance between voltage sensing electrodes (2 and 3) (m), $\sigma_b$ is the conductivity of blood (S/m), $G(t)$ is the measured instantaneous conductance (S), and $G_p$ is the parallel conductance (S) in cardiac muscle ($G_p$=0 in the calibration cuvette of FIG. 1).

Two limitations inherent in the state-of-the-art technique interfere with accurate measurements: 1) the electric field around the sensing electrodes 18 is not uniform, leading to a non-linear relationship between measured conductance and ventricular volume which has decidedly lower sensitivity to large volumes, and 2) the parallel conductance signal added by surrounding cardiac muscle adds virtual volume to the measurement. The new technique improves the estimate of the parallel muscle conductance based on the measurement of complex admittance at two or more frequencies, rather than using the admittance magnitude, as is presently done. Furthermore, the inherent non-linearity of conductance vs. volume is usually compensated by establishing a piece-wise linear approximation to the sensitivity curve (Vol vs. G) in the region of operation. That is, $\alpha$ is actually a function of the diameter of the volume in FIG. 1; but is assumed constant over the operating range of a measurement, ESV to EDV.

The electrical properties of cardiac muscle are frequency-dependent [6-14] while those of blood are not [15-18]. The admittance measurement at (at least) two frequencies can be used to separate the muscle component from the combined muscle-blood signal. Measurement of the phase angle of the admittance is a more sensitive indicator of the muscle signal than the magnitude of the admittance, which is currently measured. Information contained in the phase angle can improve the overall accuracy of the dual frequency admittance system. This reformulation of the measurement allows one to verify that the effective sensing volume actually reaches the ventricular muscle in the case of an enlarged heart.

Figure 2:
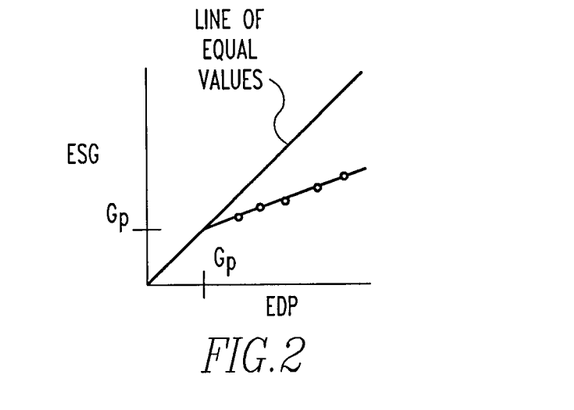
FIG. 2 is a plot for estimating parallel conductance.

In the operation of the invention, the parallel conductance signal is presently compensated by three methods: 1) hypertonic saline injection [19, 20], 2) occlusion of the inferior vena cava (IVC) [21], and 3) conductance measurement at two frequencies [22, 23]. In the first approach, a known volume of hypertonic saline (usually 10% NaCl) is injected and the beat-by-beat conductance signal measured as it washes through the LV during several beats. The End Diastolic Conductance (EDG) is plotted against End Systolic Conductance (ESG), and the resulting line is projected back to the line of equal values (EDG=ESG when stroke volume=0), and the remainder is the estimate of parallel conductance, $G_p$. (see FIG. 2.). In the second approach, occlusion of the IVC, shrinks the LV volume, but the result is analyzed in the same way as FIG. 2. The third approach attempted to use the frequency dependence of muscle to identify the parallel conductance [22, 23]. This is similar to the approach described here, but different in that the particular frequencies were limited to a maximum of about 30 kHz and only the magnitude of the combined signal was used. A maximum frequency of 100 kHz is used here to better separate the muscle from the combined signal; further, the phase angle is a much more sensitive indicator of muscle than admittance magnitude alone.

Each of the parallel conductance compensation approaches has undesirable features. Hypertonic saline injection creates an aphysiologic electrolyte load that is undesirable in the failing heart. IVC occlusion brings the ventricular free wall and septum closer to the electrode array and artificially inflates the parallel conductance. The dual frequency measurements are able to identify a difference signal between blood and cardiac muscle, but measurement using the magnitude of admittance alone is not sufficiently sensitive to yield satisfying results, and the particular frequencies used in the past are not the best to separate the two signals. There are other considerations in the dual-frequency measurement which affect overall accuracy—notably the parasitic impedances in the catheter 12 itself—which must be compensated before reliable calculations may be made. The present invention is a significant improvement to the dual frequency method; it uses measurements of the complex admittance to more accurately identify the parallel muscle volume signal and does not require injecting fluids or changing the LV volume to complete.

Frequency Dependence of Muscle Electrical Properties: Electrolytic solutions, blood and all semiconducting materials have an electrical conductivity, $\sigma$, that is essentially independent of frequency. Dielectric materials have an electric permittivity, $\varepsilon$ (F/m): in essence, permittivity is a measure of the polarizable dipole moment per unit volume in a material [14]. A general material has both semiconducting and dielectric properties, and each aspect contributes to the total current density vector, $J_{tot}$ (A/m$^2$) in a vector electric field, E (V/m). The conductivity, $\sigma$, results in conduction current density according to Ohm's Law, and the permittivity, $\varepsilon$, contributes "displacement" current density in a harmonic (i.e. sinusoidal) electric field, as reflected in the right hand side of Ampere's Law [40]:

$$J_{tot} = (\sigma + j\omega\varepsilon)E \quad (2)$$

where: $j=\sqrt{-1}$, and $\omega=2\pi f$=the angular frequency (r/s). $J_{tot}$ is complex even if E is real—in other words, J and E are not in phase with each other unless $\omega\varepsilon$ is small with respect to $\sigma$. Most all tissues behave as semiconductors at all frequencies below about 10 MHz because $\sigma \gg \omega\varepsilon$. The remarkable exception is muscle tissue in vivo or very freshly excised, [10-12, and our own unpublished measurements]. To calibrate this discussion, water has a very strong dipole moment, and has a relative permittivity of around 80 at frequencies below about 1 MHz; and the relative permittivities of most tissues are, therefore, usually dominated by their water content. Muscle, in contrast, has a very high relative permittivity: around 16,000 in the 10 kHz to 100 kHz range (almost 200 times that of water) [11], owing to the transmembrane charge distribution. Consequently, $\omega\varepsilon$ are able to observe the frequency dependence of muscle total current density since $\omega\varepsilon$ is larger than $\sigma$ for frequencies above about 15 kHz.

Figure 3:
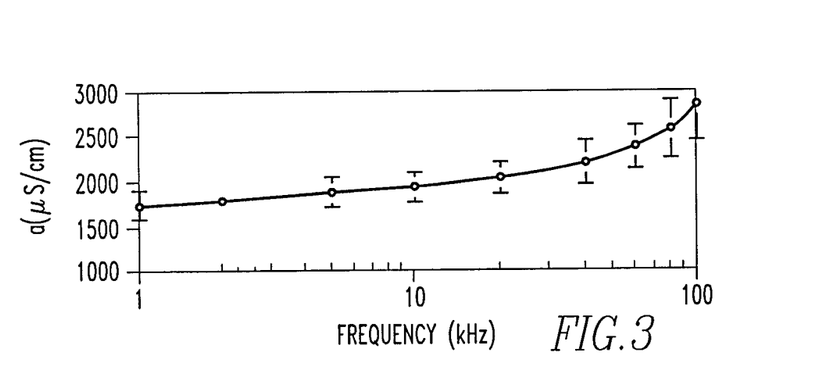
FIG. 3 is a plot of apparent conductivity of cardiac muscle as a function of frequency in CD1 mice in vivo at 37° C.

For example, the apparent conductivity of murine cardiac muscle using a surface tetrapolar probe shows a reliable and repeatable frequency dependence. In FIG. 3, the indicated conductivity increases significantly above about 10 kHz. The conductivity in the figure includes some permittivity effects: the measurement device actually indicates the magnitude of the ($\sigma+j\omega\varepsilon$) term in equation 2. For muscle, it is more accurate to think in terms of "admittivity", $\eta=\sigma+j\omega\varepsilon$. $\sigma$=1,800 µS/cm (0.18 S/m) from the low frequency portion of the plot, and estimate that $\varepsilon$=16,000 $\varepsilon_0$ (F/m) which compares well with published data. In the figure, the parasitic capacitances of the surface probe have been compensated out using measurements of the surface probe on electrolytic solutions with the same baseline conductivity as muscle.

Numerical Model Studies: Numerical models of the murine catheter in a mouse LV were executed at volumes representative of the normal ESV and EDV in the mouse. The numerical model was an enhanced version of the model used for the cuvette studies: each control volume (CV) could be assigned a different value of electrical conductivity, $\sigma$. The model spatial resolution and FDM calculational approach were the same as described above. A larger number of iterations were required for convergence, however, around 400,000 iterations. This is because the electrical boundary conditions of the inhomogeneous media substantially increase the number of trials required to settle to the final solution. Models were completed using realistic volumes for ESV and EDV derived from conductance catheter 12 data: 19 µl and 45 µl, respectively (ejection fraction=60%). Electrical conductivities for blood, cardiac muscle and aorta were: $\sigma_b$=0.928 S/m, $\sigma_m$=0.0945 S/m at 10 kHz and 0.128 S/m at 100 kHz, $\sigma_a$=0.52 S/m [41], respectively. All of the properties are real-valued in the model—the complex nature of muscle has not been included in the preliminary studies. The ventricular free wall endocardial surface was treated as a smooth ellipse, and the LV was modeled as an ellipsoid of revolution. The geometry was considerably simplified over the actual LV for two reasons: 1) the purpose of the model was to identify the expected order-of-magnitude of muscle contribution to the measured conductance, 2) the resources and time available did not permit development of a detailed 3-D geometry, nor the use of more accurate finite element method (FEM) models.

Table 1 compares FDM model and experiment data. The model consistently under-estimates the measured conductances: by about 11% and 35% at 10 kHz, and by 30% and 47% at 100 kHz. The comparisons at 10 kHz are least sensitive to uncertainty in tissue electrical properties and catheter 12 effects. Deviations at this frequency are more likely due to geometric simplifications in the model and under-estimation of the appropriate LV volume to use.

TABLE 1

Summary of model and experimental conductance values (µS). Experimental data are the means of six normal mice [28], numbers in parentheses are standard deviations.

| Source | EDV | ESV |
| --- | --- | --- |
| FDM Model @ 10 kHz | 1419 µS | 844 µS |
| Experiment @ 10 kHz | 1600 (500) | 1300 (400) |
| FDM Model @ 100 kHz | 1493 | 905 |
| Experiment @ 100 kHz | 2100 (400) | 1700 (400) |

The 100 kHz measurements reveal an additional effect due to the complex nature of the electrical properties of muscle and the effect of capacitance between the wires in the conductance catheter 12. While the actual values of the calculated conductance are subject to many uncertainties, the differences between 10 kHz and 100 kHz values in the model are due only to the electrical properties of muscle. So, in Table 1 it looks at first glance as though the model work has severely underestimated the capacitive effects in muscle. However, it must be noted that the reported in vivo measurements do not compensate out the stray capacitance in the catheter 12 at 100 kHz. At this point, it is not clear precisely how much of the apparent frequency-dependent signal is due to catheter 12 capacitance, and how much is due to muscle signal in those data.

The improved muscle parallel conductance compensation technique described can be implemented in existing conductance machines either in embedded analysis software (real-time or off-line processing of measured data) or in dedicated Digital Signal Processing hardware devices.

Phase Angle Measurement: There is an embedded difficulty in this measurement which must be addressed: the parasitic capacitance of the catheters has effects on the measured admittance signal phase angle in addition to the muscle permittivity component. One necessarily measures the two together; and a method for compensating out or otherwise dealing with the catheter-induced effects is required. Fortunately, all of the necessary catheter 12 characteristics can be measured a priori. We have identified three approaches to this problem.

Figure 4:
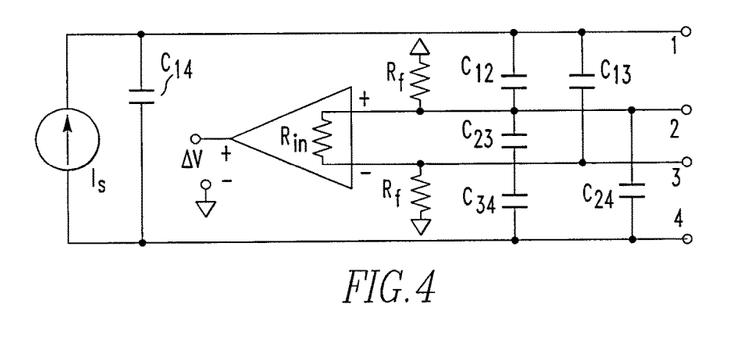
FIG. 4 shows a circuit diagram of a catheter and a measurement system for an open circuit load. The small triangles are the common node for the instrument power supply.
Figure 5:
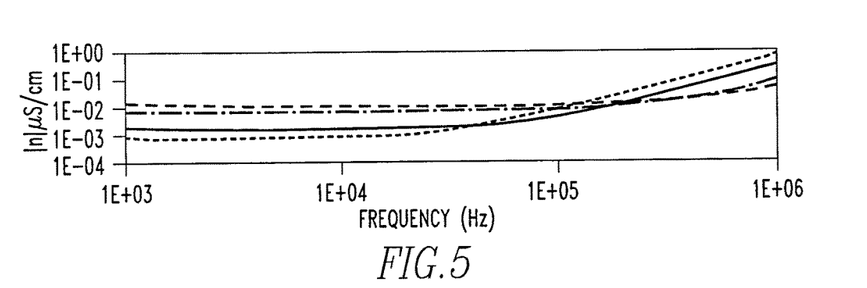
FIG. 5 is a plot of catheter phase effects for saline solutions from 720 to 10,000 μS/cm from 1 kHz to 1 MHz. Apparent conductivity ($|\eta|$) of saline solutions (μS/cm).

First, the catheter 12 phase angle effects stem from parasitic capacitance between electrode wires in the catheter 12. The tetrapolar case is relatively easy to discuss, and the multi-electrode catheters consist of several repeated combinations of the 4-electrode subunit. We can measure the six inter-electrode parasitic capacitances of the 4-electrode systems (FIG. 4). The effect of the inter-electrode capacitances can be reduced to a single capacitive admittance in parallel with the tissues, $C_{cath}$, much larger than any of the $C_U$. This can be seen in experimental measurements on saline which has no observable permittivity effects at frequencies below about 200 MHz; thus, all capacitance information (frequency-dependent increase in $|\eta|$, where $\eta=\sigma+j\omega\varepsilon$) in the signal comes from catheter 12 effects (FIG. 5). In FIG. 5 a small conductivity measurement probe (inter-electrode capacitances from 60 to 70 pF) has been used to measure the apparent conductivity ($|\eta|$) of saline solutions between 720 µS/cm (lowest line) and 10,000 µS/cm (highest line). The lines cross because the point where $\sigma_{NaCl}=\omega\varepsilon_{cath}$ moves to higher frequency for higher $\sigma$. $C_{cath}$ is approximately 1.5 nF here.

Second, a lumped-parameter circuit model can be constructed for catheter 12 effects and use this model to correct the measured potential, $\Delta V$, to the value it would have in the absence of the parasitic capacitances. Third, we can advance the measurement plane from the current-source output, $I_s$, (FIG. 5) and voltage measurement location, $\Delta V$, to the outside surfaces of the four electrodes 18 using a bilinear transform. This is a standard approach in impedance measurement [see ref. 14, Ch. 5] and requires only a measurement at open circuit, short circuit and a normalizing load (say, 1 kΩ) to accomplish.

The first approach is the most practical for implementation in a clinical instrument: we will subtract the catheter 12 capacitance, $C_{cath}$, (measured a priori) from the total capacitance of the measurement, $C_{tot}$, with the remainder: $C_{muscle}=C_{tot}-C_{cath}$. The measurement from 2 to 10 kHz includes only the real parts: $Y_{10}=G_b+G_{musc}$. At 100 kHz: $Y_{100}=G_b+G_{musc}+j\omega(C_{cath}+C_{musc})$. Negative values are rejected and $C_{cath}$ is deterministic and not time-varying. The calculation strategy is then: $C_{tot}=|Y_{100}| \sin(\theta_{tot})/\omega$; $C_{musc}=C_{tot}-C_{cath}$; finally, $G_p=G_{musc}=\sigma_m C_{musc}/\varepsilon_{musc}$ (from the well known conductance-capacitance analogy [40]) and $G_p$ can be subtracted from $|Y_{10}|$ to determine $G_b$—i.e. $|Y_{10}|=G_b+G_p$. A purely analog approach to this measurement is impossible, and a mixed signal approach with extensive digital processing required for both catheter 12 compensation and phase measurement is used. Based on the model trends and measured values of Table 1, it is estimated the relative phase angles in the measured admittance ought to be approximately 4° for EDV and 8° for ESV. The larger phase angle for ESV reflects the change in relative proximity of the LV wall.

The non uniformity of the electrode sensing field is inherent in the single current source electrode geometry of FIG. 1. Two limiting cases illustrate the origin of this. First, for a sufficiently large cuvette or blood volume, the electric and current density fields surrounding electrodes 1 and 4 are similar in overall shape to those of a current dipole: the magnitude of the current density decreases with the cube of the radius. At very large volume the voltage measured between electrodes 2 and 3 is insensitive to the location of the outer boundary. Consequently, the measured conductance saturates at large volumes since the sensitivity, $\Delta G/\Delta \text{Vol}=0$, and thus $\alpha=$zero. Second, the other limit is reached when the outer radius of the volume is minimally larger than the catheter 12 itself. In that case the current density approaches a uniform distribution and a approaches 1. Radii between these limits cross over from $\alpha=1$ to $\alpha=0$.

The behavior of a was studied in experiments and numerical models of a mouse-sized 4-electrode conductance catheter 12 in a volume-calibration cuvette. This catheter 12 has L=4.5 mm between the centers of electrodes 2 and 3 and is 1.4 F (i.e. 0.45 mm in diameter). The cuvette was filled with 1M saline solution ($\sigma=1.52$ S/m at room temperature). The results are summarized in FIG. 3. In the Figure, "Ideal G" is the line $\alpha=1$. The numerically calculated (squares) and measured (circles) conductance in µS are plotted vs. cuvette volume (µl). The measurement sensitivity, $\Delta G/\Delta \text{Vol}$, in the figure $\alpha(\pi/L^2)$, and this slope asymptotically approaches 0 for volumes greater than about 150 µl for this catheter 12. This behavior is determined solely by the geometry of the current density field, and $\alpha$ is independent of the conductivity of the solution.

Figure 6:
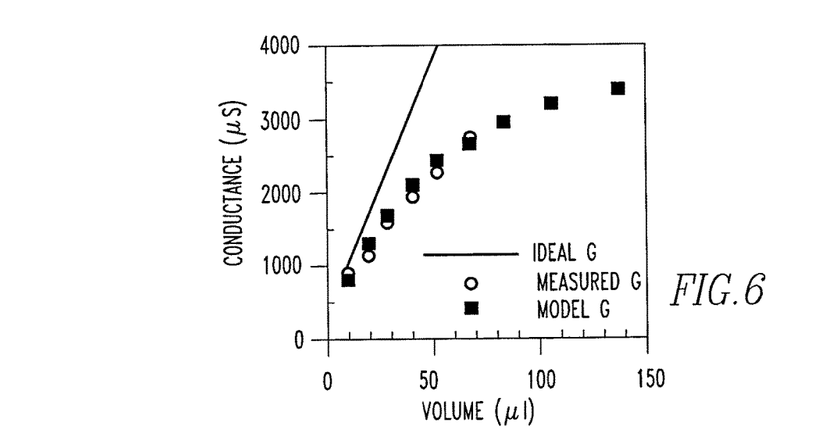
FIG. 6 is a plot of conductance vs. volume in mouse-sized calibration cuvette.

Based on the numerical model and experimental results, a new calibration equation using $\beta(G)$ as the geometry calibration function to replace a in equation 4:

$$Vol(t) = [\beta(G)]\left[\frac{L^2}{\sigma_b}\right][Y(t)-Y_p] \quad (4)$$

where: $\beta(G)=$the field geometry calibration function (dimensionless), $Y(t)=$the measured combined admittance, $\sigma_b$ is blood conductivity, L is distance between measuring electrodes, and $Y_p=$the parallel "leakage" admittance, dominated by cardiac muscle. At small volumes, $\beta(G)=\alpha=1$. At large volumes, $\beta(G)$ increases without bound, as expected from the model work in FIG. 6. The new calibration function includes the non-linear nature of the volume calculation: since for a particular catheter $\beta(G)$ depends on the conductivity of the liquid and on measured G—i.e. on cuvette and/or ventricular blood outer radius—it is not simply expressible in terms of $1/\alpha$. The expression for $\beta(G)$ for the mouse-sized catheter 12 described above for FIG. 6 data is:

$$\beta(G)(\sigma=0.928 \text{ S/m})=1+1.774(10^{481\times10^{-4}(G-2057)}) \quad (5)$$

where: G is the measured conductance (S), the calculations have been corrected to the conductivity of whole blood at body temperature (0.928 S/m), and 2057 is the asymptotic conductance in µS when the cuvette is filled with a large volume of whole blood. Here $\beta(G)$ depends only on the real part of Y because the cuvette measurements do not contain muscle. In use, G is the real part of $[Y(t)-Y_p]$, and any imaginary part of the signal is rejected since it must come from a muscle component, or from the instrumentation. As required, β(G) approaches 1 as G becomes small compared to the asymptote, 2057 µS.

The improved calibration method can be implemented in existing conductance machines either in embedded analysis software (real-time or off-line processing of measured data) or in dedicated Digital Signal Processing hardware devices.

Complex admittance in regard to overall admittance as it relates to Y(t)-$Y_p$ is as follows.

$$Y(t) = Gb + Gm + j\omega Cm$$

$$Y_p = Gm + j\omega Cm \quad (Y_p)$$

$C_m$=capacitance component of muscle (F=Farads) ($C_m$)
ω=angular frequency (radians/second) (ω=2 πf)
Gm=conductance of muscle (S=Siemens) ($G_m$)
Gb=conductance of blood (S) ($G_b$)
Y(t)=total instantaneous measured admittance (S) (after catheter 12 effects have been compensated.
$Y_p$=total parallel admittance (everything but blood). The cardiac muscle dominates $Y_p$; and thus once $Y_p$ is known (from the measurement of phase angle—only muscle has capacitance and contributes to the phase angle) the estimate of $G_b$ can be improved and thus the volume of blood.

The following elaborates on the nonlinear relationship β(G) between conductance and volume.

1. Physical Principle:

β(G) is a nonlinear function for every admittance (conductance) catheter 12. The function depends on the number, dimensions and spacing of the electrodes 18 used, and on the electrical conductivity of the medium which it is in. β(G) is determined by the shape of the current field created by the electrodes 18.

2. Experimental Determination

β(G) may be determined experimentally for any conductance catheter 12 in cylindrical "cuvettes" in which a solution of known electrical conductivity is measured over a range of cuvette diameters. The "volume" is the volume of solution between the voltage sensing electrodes 18.

3. Determination by Solution of the Electric Field Equations

β(G) may also be determined by solving the governing electric field equations, namely Gauss' Electric Law—either in integral form or in the form of the Laplace at low frequency, and the wave equations at high frequency—subject to appropriate boundary conditions. The solution may be by analytical means (paper and pencil) or by numerical means, as in a digital computer 24 model of the electric and/or electromagnetic fields. For any current field established by two or more electrodes 18 a model yields the measured conductance when the total current—surface integral of (sigma mag(E) dot product dS), where dS is the elemental area—is divided by the measurement electrode voltage, from the model or calculation results. Many books on electromagnetic field theory teach how to make the calculation. A specific reference is Chapter 6 (p. 184) in W. H. Hayt and J. A. Buck "Engineering Electromagnetics", 6th Edition McGraw-Hill, Boston, 2001, incorporated by reference herein. The specific reference teaches how to calculate resistance, R, but conductance, G is simply the reciprocal of R, G=1/R. The calculated G may be a complex number (for mixed materials like tissues), in which case the catheter 12 measures "admittance", Y, a complex number.

(A) Measured Conductance and Capacitance Signals

Two of the catheter electrodes (#1 and #4) are used to establish a current field in the ventricle. The current field results in an electric field in the tissues, the strength of which is determined by measuring the voltage between electrodes #2 and #3. Because electrodes 2 and 3 carry negligible amounts of current, they provide a useful estimate of the electric field in the tissues.

The current supplied to the tissue (electrodes 1 and 4) is divided by the voltage measured between electrodes 2 and 3 to determine the admittance of the tissue, Y (S). The admittance consists of two parts, the Conductance, G (S) the real part, and the Susceptance, B (S), the imaginary part: Y=G +jB. In this measurement, both blood and muscle contribute to the real part of the measured signal, G=$G_b$+$G_{musc}$. However, after all catheter-induced effects have been removed, only the muscle can contribute to the imaginary part, B=jω $C_{musc}$.

For any geometry of electric field distribution in a semi-conducting medium, the conductance may be calculated from:

$$G = \frac{I}{V} = \frac{\int\int_S \sigma E \bullet dS}{-\int_a^b E \bullet dl} \quad (a)$$

where the surface, S, in the numerator is chosen to enclose all of the current from one of the electrodes used to establish the electric field, E, and the integration pathway in the denominator is from the low voltage "sink" electrode at position "a" to the higher voltage "source" electrode at position "b". Similarly, for any geometry of electric field in a dielectric medium, the capacitance may be calculated from:

$$C = \frac{Q}{V} = \frac{\int\int_S \varepsilon E \bullet dS}{-\int_a^b E \bullet dl} \quad (b)$$

B) Parallel Admittance in the Cardiac Muscle

The measured tissue signal, Y=$G_b$+$G_{musc}$+kω$C_{musc+}$. From the high frequency measurement $C_{musc}$ may be determined from the measured phase angle by: $C_{musc}$=|Y| sin (θ)/ω after catheter phase effects have been removed. By equations (a) and (b) above, the muscle conductance can be determined from its capacitance by: $G_{musc}$=σ/ε $C_{musc}$ since the two equations differ only by their respective electrical properties—i.e. the electric field geometry calculations are identical in a homogeneous medium. In this way, the muscle conductance (independent of frequency, and thus the same in the low frequency and high frequency measurements) may be determined from the muscle capacitance (observable only in the high frequency measurements).

Beyond these very general relations, a person may make catheter electrode configurations of many shapes and sizes and use them in many sorts of conductive solutions. All would have a different β(G) function.

In an alternative embodiment, the LV volume signal is only relative to LV blood conductance, but the measured admittance comes from both blood and myocardium. Therefore, it is desired to extract the blood conductance from the measured admittance, which can be done by using the unique capacitive property of myocardium. To achieve it, the first step is to obtain the conductivity and permittivity of myocardium.

Myocardial Conductivity and Permittivity

It is believed that blood is only conductive, while myocardium is both conductive and capacitive. Therefore, the measured frequency-dependent myocardial "admittivity", $Y'_m(f)$, actually is composed of two components:

$$Y'_m(f) = \sqrt{\sigma_m^2 + (2\pi f \varepsilon_r \varepsilon_0)^2} \quad (6)$$

where $\sigma_m$ is the real myocardial conductivity, f is frequency, $\varepsilon_r$ is the relative myocardial permittivity, and $\varepsilon_0$ is the permittivity of free space. Experimentally, $Y'_m(f)$ can be measured at two different frequencies, such as 10 and 100 kHz, and then the value of $\sigma_m$ and myocardial permittivity $\varepsilon$ can be calculated by:

$$\sigma_m = \sqrt{\frac{100 \cdot [Y'_m(10k)]^2 - [Y'_m(100k)]^2}{99}} \quad (7)$$

$$\varepsilon \equiv \varepsilon_r \varepsilon_0 = \frac{1}{2\pi \cdot 10^4} \sqrt{\frac{Y'_m(100k)]^2 [Y'_m(10k)]^2}{99}} \quad (8)$$

Blood Conductance

In the 10 and 100 kHz dual-frequency measurement system, the measured magnitude of admittance, $|Y(f)|$, is blood conductance ($g_b$) in parallel with myocardial conductance ($g_m$) and capacitance ($C_m$), shown as $$|Y(10k)| = \sqrt{(g_b + g_m)^2 + (2\pi \cdot 10^4 C_m)^2} \quad (9)$$

$$|Y(100k)| = \sqrt{(g_b + g_m)^2 + (2\pi \cdot 10^5 C_m)^2} \quad (10)$$

Using equations (9) and (10), $$C_m = \frac{1}{2\pi \cdot 10^4} \sqrt{\frac{|Y(100k)|^2 - |Y(10k)|^2}{99}} \quad (11)$$

$$g_b + g_m = \sqrt{\frac{100 \cdot |Y(10k)|^2 - |Y(100k)|^2}{99}} \quad (12)$$

From the well known conductance-capacitance analogy [40], $$g_m = C_m \frac{\sigma_m}{\varepsilon} \quad (13)$$

Substitute eq. (13) into eq. (12), blood conductance $g_b$ is obtained as $$g_b = \left( \sqrt{\frac{100 \cdot |Y(10k)|^2 - |Y(100k)|^2}{99}} \right) - g_m \quad (14)$$

A new conductance-to-volume conversion equation is $$\text{Vol}(t) = \rho_b L^2 g_b(t) \exp[\gamma \cdot (g_b(t))^2] \quad (15)$$

where Vol(t) is the instantaneous volume, $\rho_b$ is the blood resistivity, L is the distance between the sensing electrodes, $g_b(t)$ is the instantaneous blood conductance, and $\gamma$ is an empirical calibration factor, which is determined by the following steps.

1. A flow probe is used to measure the LV stroke volume (SV), denoted as $SV_{flow}$.
2. Assign an initial positive number to $\gamma$, and use equation (15) to convert blood conductance to volume signal. The resulting stroke volume is denoted as $SV\gamma$.
3. If $SV\gamma$ is smaller than $SV_{flow}$, increase the value of $\gamma$. Otherwise, decrease it.
4. Repeat steps 2 and 3 until it satisfies.

$$SV\gamma - SV_{flow} \quad (16)$$

Since equation (15) is a monotonic increasing function, there is only one possible positive solution for $\gamma$.

This empirical factory is used to compensate and calibrate the overall uncertainty and imperfection of the measurement environment, such as inhomogeneous electrical field and off-center catheter position.

Simulation Results

Figure 8:
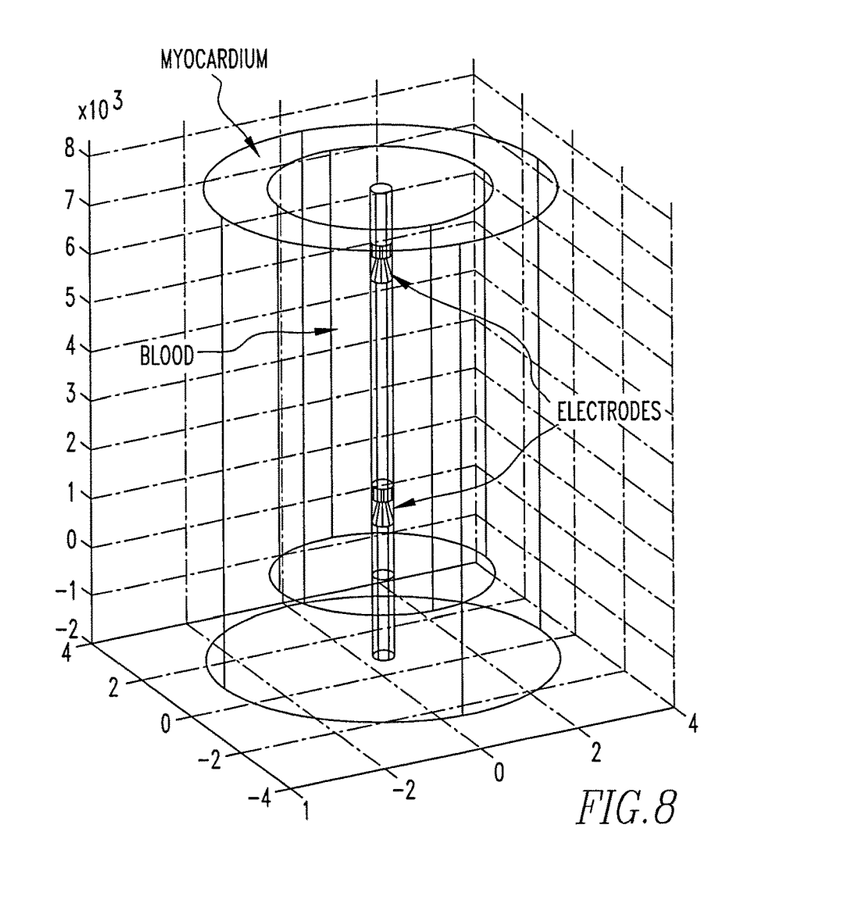
FIG. 8 is a cylinder-shaped murine LV model: both blood and myocardium are modeled as cylinders.

A commercial finite element software, FEMLAB, is used to simulate this problem. A simplified LV model is created by modeling both LV blood and myocardium as cylinders with a four-electrode catheter inserted into the center of cylinders, as shown in FIG. 8.

Figure 9:
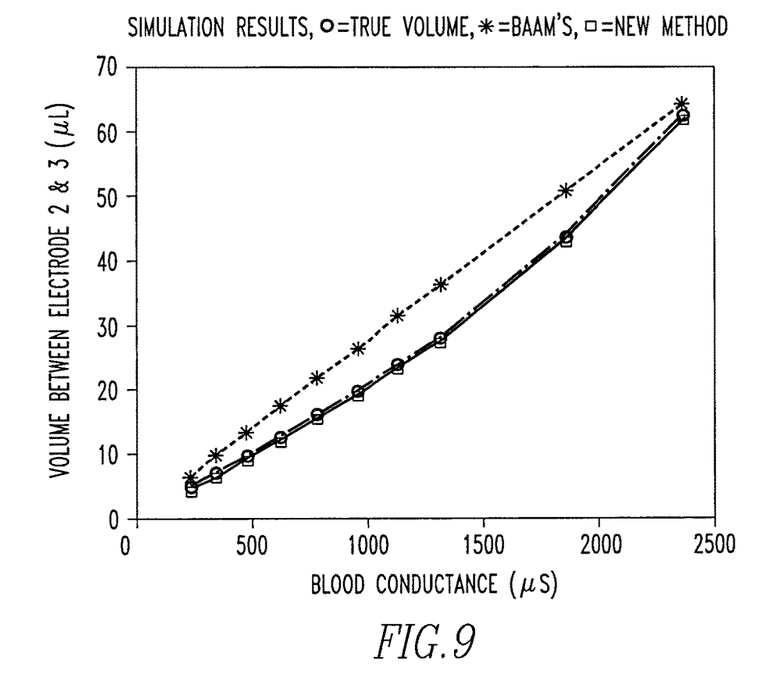
FIG. 9 is a comparison between true volume and estimated volume by the new and Baan's equations in FEMLAB simulations.

The radius of the inner blood cylinder was changed to explore the relationship between volume and conductance. Assuming stroke volume is the difference between the largest and smallest blood volume, and this difference is used to determine the empirical calibration factors, $\alpha$ and $\gamma$, for Baan's and the new equations respectively. The calculated magnitude of admittance, blood conductance, true volume, and estimated volume by Baan's and the new equations are listed in Table II and also plotted in FIG. 9, where the true volume is the volume between the two inner sensing electrodes. The distance between two inner sensing electrodes for a mouse size catheter is 4.5 mm.

TABLE II

Comparison of true and estimated volume by two equations

| Calculated magnitude of admittance (μS) | Blood conductance (μS) | True volume (μL) | Estimated volume by Baan's equation (μL) | Estimated volume by new equation (μL) |
|---|---|---|---|---|
| 2491.1 | 2344.7 | 62.9 | 64.5 | 62.0 |
| 2030.2 | 1853.3 | 43.7 | 51.0 | 43.1 |
| 1514.0 | 1314.3 | 28.0 | 36.2 | 27.5 |
| 1337.7 | 1133.5 | 23.5 | 31.2 | 23.0 |
| 1162.4 | 956.1 | 19.4 | 26.3 | 19.0 |
| 992.5 | 786.4 | 15.7 | 21.6 | 15.3 |
| 829.3 | 626.2 | 12.4 | 17.2 | 12.0 |
| 677.3 | 479.3 | 9.5 | 13.2 | 9.1 |
| 538.1 | 347.9 | 7.0 | 9.6 | 6.6 |
| 414.4 | 234.2 | 4.9 | 6.4 | 4.4 |

In Vitro Saline Experiments

Several cylinder holes were drilled in a 1.5-inch thick block of Plexiglas. The conductivity of saline used to fill those holes was 1.03 S/m made by dissolving 0.1 MNaCl in 1 liter of water at 23° C. room temperature, which is about the blood conductivity. A conductance catheter with 9 mm distance between electrodes 2 and 3 is used to measure the conductance.

Figure 10:
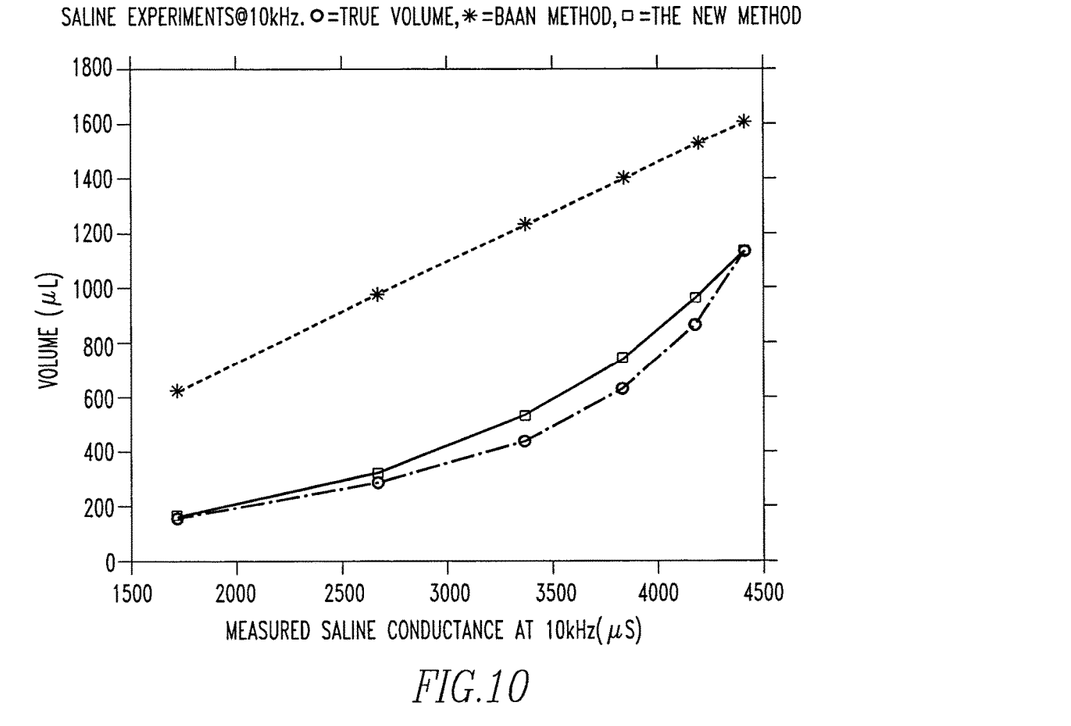
FIG. 10 is a comparison between true volume and estimated volume using the new and Baan's equations in saline experiments.

Since plexiglas is an insulating material, the measured conductance comes from saline only, not from the plexiglas wall. Therefore, the measured saline conductance corresponds to the blood conductance in vivo experiments. Again, stroke volume is assumed to be the difference between the largest and smallest blood volume, and then used to determine the empirical calibration factors, $\alpha$ and $\gamma$, for Baan's and the new equations, respectively. The measured data at 10 kHz and the estimated volume by Baan's and the new equations are listed in Table III. The true volume listed is the volume between electrodes 2 and 3. The data are plotted in FIG. 10.

TABLE III

Comparison of true and estimated volume in the drilled holes

| Diameter of Drilled holes (inch) | Measured conductance (µS) | True volume (µL) | Estimated volume by Baan's equation (µL) | Estimated volume by new equation (µL) |
|---|---|---|---|---|
| 3/16 | 1723.5 | 160.3 | 562.0 | 160.5 |
| 1/4 | 2675.0 | 285.0 | 872.3 | 310.3 |
| 5/16 | 3376.0 | 445.3 | 1100.9 | 494.5 |
| 3/8 | 3836.4 | 641.3 | 1251.0 | 684.8 |
| 7/16 | 4171.0 | 827.9 | 1360.1 | 866.7 |
| 1/2 | 4394.3 | 1140.1 | 1432.9 | 1031.2 |

It is found that the resulting volumes obtained from the new equation are much closer to the MRI data, which is believed to be the truth. However, more noise is found in a larger volume by the new method, observed in FIG. 11. The reason is that as the volume increases, the exponential term of the new equation would amplify the noise more rapidly than the linear Baan's equation.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

APPENDIX

The following is a list of references, identified herein, all of which are incorporated by reference herein.
1. Baan, J., Jong, T., Kerkhof, P., Moene, R., vanDijk, A., van der Velde, E., and Koops, J.; Continuous stroke volume and cardiac output dam intra-ventricular dimensions obtained with impedance catheter. Cardiovascular Research, v15 pp328-334, 1981.
2. J. Baan, E. van der Velde, H. deBruin, G. Smeenk, J. Koops, A. vanDijk, D. Temmerman, J. Senden, and B. Buis; Continuous measurement of left ventricular volume in animals and humans by conductance catheter. Circulation, v70 n5, pp812-823, 1984.
3. Burkhoff D, Van Der Velde E, Kass D, Baan J, Maughan W L, Sagawa K. Accuracy of volume measurement by conductance catheter in isolated, ejecting canine hearts. Circulation 72:440-447,1985.
4. MacGowan G A, Haber H L, Cowart T D, Tedesco C, Wu C C, Feldman M D. Direct myocardial effects of OPG-18790 in human heart failure: beneficial effects on contractile and diastolic function demonstrated by intracoronary infusion with pressure-volume analysis. JACC 31;1344-1351, 1998.
5. Steendijk, P., Mur, G., Van der Velde, E. and Baan, J.; The four-electrode resistivity technique in anisotropic media: theoretical analysis and application in myocardial tissue in vivo. IEEE Trans. on Biomed. Engr., v40, n11, pp1138-1148, 1993.
6. Sperelakis, N and Hoshiko, T.; Electrical impedance of cardiac muscle. Circ. Res. v9 pp1280-1283,1961.
7. Richard D Stoy; Kenneth R Foster, Herman P Schwan; Dielectric properties of mammalian tissues from 0.1 to 100 MHz: a summary of recent data. Physics in Medicine and Biology, v27 n4 pp 501-513, 1982.
8. Steendijk, P., Mur, G., Van der Velde, E and Baan, J.; The four-electrode resistivity technique in anisotropic media: theoretical analysis and application in myocardial tissue in viva. IEEE Trans. on Biomed. Engr., v40, n11, pp1138-1148, 1993.
9. Steendijk, P., Mur, G., Van der Velde, E and Baan, J.; Dependence of anisotropic myocardium electrical resistivity on cardiac phase and excitation frequency. Basic Res. Cardiol., v89, pp411-426, 1994.
10. Gabriel C; Gabriel S; Corthout E; The dielectric properties of biological tissues: I. Literature survey. Physics in Medicine and Biology v 41, n11, pp 2231-2249, 1996.
11. Gabriel S; Lau RW; Gabriel C; The dielectric properties of biological tissues: II. Measurements in the frequency range 10 Hz to 20 Ghz. Physics in Medicine and Biology v41 n11, pp 2251-2269, 1996.
12. Gabriel, S; Lau RW; Gabriel C; The dielectric properties of biological tissues: III. Parametric models for the dielectric spectrum of tissue. Physics in Medicine and Biology, v41, n11, pp2271-2293, 1996.
13. Tsai, J-Z, Will, J. A., Hubard-van Stelle, S., Cao, H., Tungjitkusolmun, S., Choy, Y. B., Haemmerich, D., Vorperian, V. R., and Webster, J. G.; In-vivo measurement of swine myocardial resistivity. IEEE Trans. Biomed. Engr., v49, n5, pp472-483, 2002.
14. Tsai, J-Z, Will, J. A., Hubard-van Stelle, S., Cao, H., Tungjitkusolmun, S., Choy, Y. B., Haemmerich, D., Vorperian, V. R., and Webster, J. G.; Error analysis of tissue resistivity measurement. IEEE Trans. Biomed. Engr., v49, n5, pp484-494, 2002.

What is claimed is:

1. An apparatus for determining cardiac performance in a patient comprising:
a plurality of electrodes adapted to he placed in the patient and in communication with a heart chamber of the patient for measuring conductance and blood volume in the heart chamber of the patient and acquiring a measurement of admittance; and
a processor for determining instantaneous blood volume of the ventricle based on measurement of admittance to identify mechanical strength of the chamber, the processor in communication with the electrodes.

2. An apparatus as described in claim 1 wherein the processor produces a plurality of desired wave forms at desired frequencies for the electrodes.

3. An apparatus as described in claim 2 wherein the processor produces the plurality of desired wave forms at desired frequencies simultaneously, and the processor separates the plurality of desired wave forms at desired frequencies the processor receives from the electrodes.

4. An apparatus as described in claim 3 wherein the plurality of electrodes is disposed on a conductance catheter to measure a least one segmental volume of the heart chamber.

5. An apparatus as described in claim 4 wherein the pressure sensor is in contact with the conductance catheter to measure ventricular pressure in the chamber.

6. An apparatus as described in claim 5 including a pressure sensor for measuring instantaneous pressure of the heart chamber in communication with the processor.

7. An apparatus as described in claim 6 wherein the plurality of electrodes includes intermediate electrodes to measure and instantaneous voltage signal from the heart, and outer electrodes to which a current is applied from the processor.

8. An apparatus as described in claim 7 wherein the pressure sensor is disposed between the intermediate electrodes and the outer electrodes.

9. An apparatus as described in claim 8 wherein the processor includes a computer with a signal synthesizer which produces the plurality of desired wave forms at desired frequencies and a data acquisition mechanism for receiving and separating the plurality of desired wave forms at desired frequencies.

10. A method for determining cardiac performance in a patient comprising the steps of:
    measuring conductance and blood volume in a heart chamber of the patient and acquiring a measurement of admittance with a plurality of electrodes disposed in the patient and in communication with the heart chamber; and
    determining instantaneous volume of the ventricle based on measurement of admittance to identify mechanical strength of the chamber with a processor, the processor in communication with the electrodes.

11. A method as described in claim 10 including the step of producing a plurality of desired wave forms at desired frequencies for the electrodes disposed on a conductance catheter.

12. A method as described in claim 11 wherein the producing step includes the step of producing the plurality of desired wave forms at desired frequencies simultaneously, and including the step of the processor separating the plurality of desired wave forms at desired frequencies the processor received from the conductance catheter.

13. A method as described in claim 12 wherein the producing step includes the step of producing with the processor the plurality of desired wave forms at desired frequencies simultaneously.

14. An apparatus for determining cardiac performance in a patient comprising:
    a plurality of electrodes adapted to be placed in the patient and in communication with a heart chamber of the patient for measuring blood volume in the heart chamber of the patient and acquiring a measurement of admittance; and
    a processor for determining instantaneous blood volume of the ventricle based on measurement of admittance magnitude to identify mechanical strength of the chamber, the processor in communication with the electrodes.

* * * * *